United States Patent
Matier et al.

(12) 
(10) Patent No.: US 6,197,817 B1
(45) Date of Patent: Mar. 6, 2001

(54) PHENYLPROPIONIC ACIDS AND ESTERS: COMPOUNDS AND METHODS FOR INDUCING BETA-BLOCKADE FOR THE TREATMENT OF CARDIAC DISORDERS

(75) Inventors: William L. Matier, Hockessin, DE (US); Shyam Patil, Lincoln University, PA (US)

(73) Assignee: Selectus Pharmaceuticals, Inc., Kennett Square, PA (US)

( * ) Notice: Subject to any disclaimer, the term of this patent is extended or adjusted under 35 U.S.C. 154(b) by 0 days.

(21) Appl. No.: 09/235,844

(22) Filed: Jan. 22, 1999

(51) Int. Cl.[7] ............................ A61K 31/38; A61K 31/35; A61K 31/27; A61K 31/175
(52) U.S. Cl. ..................... 514/538; 514/237.5; 514/448; 514/459; 514/471; 514/538; 514/570; 514/467; 514/486; 514/517; 514/564; 549/72; 549/425; 549/449; 549/450; 560/42; 562/451; 544/169
(58) Field of Search ................................ 560/42, 13, 24, 560/34; 562/451, 430, 439; 514/538, 570, 237.5, 448, 459, 471, 467, 486, 517, 564; 544/169; 549/72, 425, 450, 449

(56) References Cited

U.S. PATENT DOCUMENTS

| | | | |
|---|---|---|---|
| 3,888,993 | 6/1975 | Boschetti et al. | 424/309 |
| 3,961,071 | 6/1976 | Koppe et al. | 424/319 |
| 4,387,103 | * 6/1983 | Erhardt et al. | 424/309 |
| 4,402,974 | 9/1983 | Matier et al. | 424/308 |
| 4,454,154 | 6/1984 | Matier | 424/309 |
| 4,455,317 | 6/1984 | Matier | 424/309 |
| 4,578,403 | 3/1986 | Matier | 514/522 |
| 4,990,688 | * 2/1991 | Mai et al. | 564/349 |
| 5,536,749 | * 7/1996 | Matier et al. | 514/533 |

OTHER PUBLICATIONS

J.E. Shaffer et al. In Vitro and In Vivo evaluation of Two Ultrashort–Acting Beta–Adrenoreceptor Antagonists: ACC–9129 and ACC–9369. *Drug Development Research.* 1986 7:221–232.

Check Y. Sum, Ph.D., et al. Kinetics of esmolol, an ultra–short–acting beta blocker, and of its major metabolite. *Clinical Pharm Ther.* 1983 34: 427–434.

* cited by examiner

*Primary Examiner*—Peter O'Sullivan
(74) *Attorney, Agent, or Firm*—Janet E. Reed; Saul Ewing LLP

(57) ABSTRACT

Disclosed are compounds of the formula:

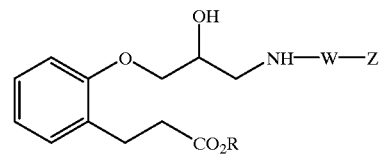

R represents hydrogen or is a C-3 to C-6 cycloalkyl or C-4 to C-10 straight or branched carbon chain alkyl-cycloalkyl or a group —B—D, where B is C-2 to C-10 straight or branched carbon chain alkyl and D is hydroxy or alkyloxy or 2,3-dihydroxypropyl or 2,3-dialkyloxypropyl or 2,2-dialkyl-1,3-dioxolane-5-methyl, where alkyl is C-1 to C-10 straight or branched carbon chain;

W represents $CH(CH_3)CH_2$—, $C(CH_3)_2CH_2$—;

Z represents hydrogen, —$NHCOR_2$, —$NHCONR_2R_3$ or —$NHSO_2R_2$ or —$NHSO_2NR_2R_3$ or —$NHCOOR_4$ wherein $R_4$ is alkyl of from 1 to about 6 carbon atoms, alkoxyalkyl wherein the alkyl groups may be the same or different and contain from 1 to about 6 carbon atoms, alkoxyaryl, cycloalkyl of from 3 to about 8 carbon atoms. $R_2$ and $R_3$ may be the same or different and represent hydrogen, alkyl of from 1 to about 6 carbon atoms, alkoxyalkyl wherein the alkyl groups may be the same or different and contain from 1 to about 6 carbon atoms, alkoxyaryl, cycloalkyl of from 3 to about 8 carbon atoms, a phenyl group substituted or unsubstituted, heteroaryl, furanyl, thiophenyl, imidazolyl, oxazolyl or indolyl or tetrahydrofuranyl, tetrahydropyranyl, dioxanyl, 2,2-dimethyl dioxolane-5-methyl, pyrrolidinyl, piperazinyl and tetrahydrooxazolyl, aralkyl except that $R_2$ and $R_3$ are not hydrogen when Z is —$NHSO2R_2$, or $R_2$ and $R_3$ may together with N form a 5 to 7 membered heterocyclic group; and pharmaceutically acceptable salts thereof; and all stereoisomeric forms, as well as racemic mixtures. The compounds in the present invention relates to compounds, methods, formulation and pharmaceutical compositions for the general treatment or prophylaxis of diseases states which are responsive to attenuation of sympathetic nervous system activity or beta adrenergic blockade namely: coronary artery disease including myocardial ischemic disorders, angina and myocardial infarction; arrhythmia; hypertension; anxiety including panic attack; migraine or glaucoma by the intravenous or sublingual or oral or topical ocular administration.

37 Claims, No Drawings

PHENYLPROPIONIC ACIDS AND ESTERS: COMPOUNDS AND METHODS FOR INDUCING BETA-BLOCKADE FOR THE TREATMENT OF CARDIAC DISORDERS

FIELD OF THE INVENTION

The present invention relates to phenylpropionic acid and ester compounds and methods for the general treatment of diseases responsive to beta adrenergic blockade or caused by activation of the sympathetic nervous system (SNS) namely: coronary artery disease, including myocardial ischemic disorders, angina and myocardial infarction; arrhythmia; hypertension; anxiety; migraine or glaucoma, by the intravenous or oral or topical ocular administration of novel beta adrenergic blocking agents. In particular, the invention relates to novel phenylpropionic acids, a method for oral administration of said compounds in the form of ester derivatives and a pharmaceutical formulation for administration of these compounds in the form of rapidly dissolving tablets. The invention also relates to a method of administering an inactive or very weakly active phenylpropionate ester topically in the eye, which produces the corresponding phenylpropionic acid upon enzymatic hydrolysis as an active beta blocker in the aqueous humor in sufficient quantities to lower intra ocular pressure (IOP).

BACKGROUND OF THE INVENTION

Various scientific articles and publications are referred to throughout the specification. These are incorporated by reference herein to describe the state of the art to which this invention pertains.

Sympathetic nervous system activation can result in increases in heart rate, blood pressure and cardiac contractility. Activities causing such a result can be physical exertion such as climbing, exercise, running or sexual intercourse. Likewise, symptoms such as sweating, tremor and palpitations can result from short-term stressful conditions which might be caused, for example, by "stage fright" because of public speaking, vocal or musical performance or phobias or panic attack. Control of heart rate, blood pressure and cardiac contractility during activities is particularly important for patients at risk due to coronary artery disease such as myocardial ischemic disorders. Severe attacks of chest pain, angina pectoris, occur when cardiac work and myocardial oxygen demand exceed the ability of the coronary arterial system to supply oxygen. The major determinants of myocardial oxygen consumption are heart rate, systolic tension (arterial pressure) and cardiac contractility. Any increase in any of these determinants in the presence of reduced coronary blood flow may induce angina. The higher the blood pressure and the faster the heart rate, the greater the unmet myocardial oxygen need. Rapid control of heart rate or blood pressure during such short term activities is particularly important for patients at risk due to coronary artery disease such as myocardial ischemic disorders. While long acting chronic, orally administrable beta blockers are available, the treatment of the conditions described often require drugs with fast onset of action and a relatively short duration of action which allows discontinuation of therapy in the event of severe side-effects. Such compounds and methods are described in the present invention.

Beta adrenergic blocking agents containing carboxylic ester groups are reported in the technical and patent literature. However, their corresponding carboxylic acids are generally taught to be inactive or only weakly active as beta blockers. Thus, a large group of ester containing compounds are reported as short-acting beta blocking agents when administered intravenously (J Med Chem. 1983, 1109–12; J Med Chem. 1982,1408; J Med Chem. 1982,1402; Life Sci. 1982,899; Pharm Res. 1995, 329; U.S. Pat. No. 4,387,103 issued on Jun. 7, 1983; U.S. Pat. No. 4,593,119, 1986 issued on Jun. 3, 1986; U.S. Pat. No. 4,692,446 issued on Sep. 8, 1987; U.S. Pat. No. 5,202,347 issued on Apr. 13, 1993) or topically as eye-drops for glaucoma (U.S. Pat. No. 4,455, 317 issued on Jun. 19, 1984; U.S. Pat. No. 4,454,154 issued on Jun. 12, 1984; U.S. Pat. No. 4,578,403 issued on Mar. 25, 1986; U.S. Pat. No. 5,202,347 issued on Apr. 13, 1993; U.S. Pat. No. 4,829,086 issued on May 9, 1989), or by sublingual, buccal and intranasal administration (U.S. Pat. No. 5,536, 749,1996). The basis for the short duration of action of these compounds was the rapid metabolism of the active esters to inactive or very weakly active carboxylic acids. (An "inactive beta blocker" is defined as a compound which is impractical to dose). The only examples of carboxylic acids with beta blocking activity are a compound with a carboxylic acid directly attached to an aromatic ring and one with a carboxylic acid conjugated with an aromatic ring (U.S. Pat. No. 3,961,071 issued on Jun. 1, 1976; and U.S. Pat. No. 3,888,993 issued on Jun. 10, 1975). No examples of ortho substituted phenyl aliphatic carboxylic acid beta blockers such as phenylpropionic acid containing compounds are known.

The drug esmolol (Physicians Desk Reference), shown below, is an intravenously infused beta blocking agent based on the "inactive metabolite" approach. It is marketed for acute treatment of cardiac disorders. This ester is rapidly metabolized in vivo to the corresponding carboxylic acid, which is reported to have an elimination half-life of 3.7 hours in man. During intravenous infusions, the acid metabolite accumulates to high concentrations in blood, but does not exhibit beta blocking activity. (Clin. Pharmacol. Ther. 34: 427–434, 1984).

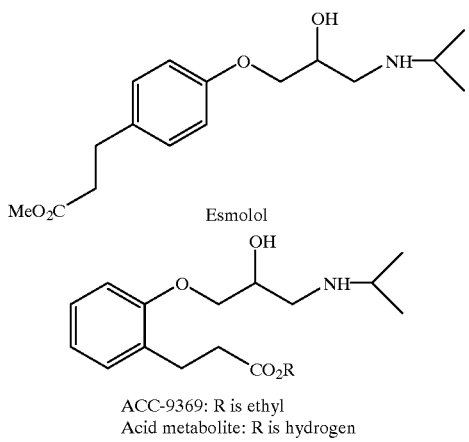

ACC-9369: R is ethyl
Acid metabolite: R is hydrogen

The ethyl ester ACC-9369, shown above, was also reported to be rapidly converted in vivo to a metabolite, with little or no beta-blocking activity in dogs (J. E. Shaffer et al, Drug Development Research, 1: 221–232, 1986).

Glaucoma is a condition of the eye characterized by an increase in intraocular pressure. Untreated, the condition can eventually lead to irreversible retinal damage and blindness. Beta blockers have been the first line of therapy to reduce the IOP. After topical application of an eye drop, conjunctival and systemic absorption of drugs is typically an order of magnitude greater than their ocular absorption. In addition substantial systemic absorption of ophthalmic drugs takes place via the nasal mucosa. Systemic absorption of beta blocking agents may cause life threatening side-effects in patients with certain cardiac and pulmonary conditions. The ideal drug will only penetrate into the inner eye in order to reduce the intraocular pressure but will not produce any effects in the systemic circulation. A method for treating glaucoma with decreased systemic side effects, by topical administration of selectively metabolized potent beta-blocking agents has been described in U.S. Pat. No. 4,402,974 issued on Sep. 6, 1983; U.S. Pat. No. 4,455,317 issued on Jun. 19, 1984; U.S. Pat. No. 4,578,403 issued on Mar. 25, 1986; U.S. Pat. No. 4,454,154 issued on Jun. 12, 1984. When these compounds are absorbed systemically, the compounds are metabolized rapidly so that systemic beta blocking effects are relatively short acting. However, the drugs may cause an initial strong beta blocking effect until metabolism occurs.

SUMMARY OF THE INVENTION

Unexpectedly, it has now been discovered that the presumed acid metabolite of ACC-9369 and related carboxylic acids are potent beta blockers in vivo in dogs and man, although weak blockers in vitro. It is believed that, because of their unique pharmacokinetic properties, the acids remain mostly in the plasma compartment and are poorly distributed into body tissues. They therefore surprisingly reach effective beta blocking concentrations in the blood after relatively low administered doses. In addition, unexpectedly, these compounds undergo rapid elimination from the blood with a half life of approximately 30–120 minutes. Also, unexpectedly, it has been discovered that oral administration of ACC-9369 and related esters, produces high blood levels of the corresponding acids, which have an onset of beta blocking action within 15–30 minutes and an elimination half life of 30 to 90 minutes in man.

It has also been discovered in accordance with the present invention that the problem of overly strong initial effects when treating glaucoma with beta blockers can be solved by dosing an inactive or very weakly active phenylpropionate ester containing beta blocker topically, which penetrates the cornea and is hydrolyzed to produce an active phenylpropionic acid beta blocker, in the aqueous humor, in sufficient quantities to lower IOP. As with other topically administered eye drops, the phenylpropionate ester is substantially absorbed into the systemic circulation but produces little or no beta blockade. These esters are then metabolized by esterases or eliminated from the blood so that they produce only low or sub-effective beta blocking concentrations of the phenyl propionic acids.

Disclosed are compounds and methods for providing rapid onset, short-duration beta-blockade in patients having coronary artery disease or for attenuating sympathetic nervous system hyperactivity or arrhythmia or migraine or ocular hypertension or anxiety including panic attack and lower IOP in patients with glaucoma. The compounds are administered intravenously or orally or ocularly. Also described is a novel pharmaceutical formulation for administration of these compounds in the form of rapidly dissolving tablets. The compounds are described by formula I:

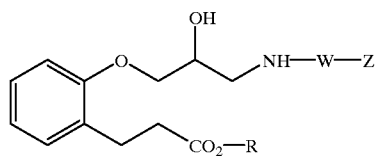

wherein:

R represents hydrogen or C-1 to C-10 straight or branched carbon chain alkyl or C-3 to C-6 cycloalkyl or C-4 to C-10 straight or branched carbon chain alkyl-cycloalkyl or a group —B—D, where B is C-2 to C-10 straight or branched carbon chain alkyl and D is hydroxy or alkyloxy or 2,3-dihydroxypropyl or 2,3-dialkyloxypropyl or 2,2-dialkyl-1,3-dioxolane-5-methyl, where alkyl is C-1 to C-10 straight or branched carbon chain;

W represents $CH(CH_3)CH_2-$, $C(CH_3)_2CH_2-$

Z represents hydrogen, $-NHCOR_2$, $-NHCONR_2R_3$ or $-NHSO_2R_2$ or $-NHSO_2NR_2R_3$ or $-NHCOOR_4$ wherein $R_4$ is alkyl of from 1 to about 6 carbon atoms, alkoxyalkyl wherein the alkyl groups may be the same or different and contain from 1 to about 6 carbon atoms, alkoxyaryl, cycloalkyl of from 3 to about 8 carbon atoms. $R_2$ and $R_3$ may be the same or different and represent hydrogen, alkyl of from 1 to about 6 carbon atoms, alkoxyalkyl wherein the alkyl groups may be the same or different and contain from 1 to about 6 carbon atoms, alkoxyaryl, cycloalkyl of from 3 to about 8 carbon atoms, a phenyl group substituted or unsubstituted, heteroaryl, furanyl, thiophenyl, imidazolyl, oxazolyl or indolyl or tetrahydrofuranyl, tetrahydropyranyl, dioxanyl, 2,2-dimethyl dioxolane-5-methyl, pyrrolidinyl, piperazinyl and tetrahydrooxazolyl, aralkyl except that $R_2$ and $R_3$ are not hydrogen when Z is $-NHSO2R_2$, or $R_2$ and $R_3$ may together with N form a 5 to 7 membered heterocyclic group; and pharmaceutically acceptable salts thereof.

DETAILED DESCRIPTION OF THE INVENTION

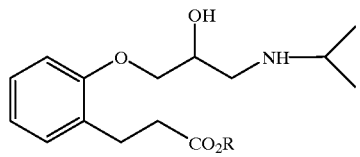

ACC-9369: R is ethyl
Acid metabolite: R is hydrogen

The concept of short-acting beta-blockers discussed in the literature is described earlier in this patent. Although an extensive array of short acting ester containing beta-blockers were studied and implied that the corresponding acid metabolites were inactive, only few metabolite acids were actually made and shown to be inactive in vitro and vivo. It is also reported that ACC-9369 is a potent beta blocker in vivo in dogs and is converted in vivo to an inactive metabolite acid. It has now been discovered that the acid metabolite of ACC-9369 is of the structure shown above and unexpectedly, upon intravenous administration of this acid to dogs it exhibited strong beta-blocking activity. This activity is presumably due to it's different pharmacokinetic properties, since it remains mostly in the plasma compartment and is poorly distributed into body tissues. Similarly, in man, the metabolite acid surprisingly reaches effective beta blocking concentrations in the blood after relatively low administered doses of ACC-9369 and it has an onset of beta blocking action within 15–30 minutes. In addition, unexpectedly, this acid form undergoes rapid elimination from the blood with a half life of approximately 90 minutes.

The present invention describes:

1. Novel propionic acid containing aryloxypropanolamine compounds described by formula I wherein R is hydrogen.
2. The method of intravenously or orally administering novel carboxylic acid containing compounds of formula I (wherein R is hydrogen), which have a systemic half life of approximately 30–120 minutes.
3. The method of administering by the oral route specific esters of formula I which produce a therapeutic effect (beta-blockade) within 15–30 min and which have a systemic half life of approximately 30–120 minutes.
4. The method of treating glaucoma or lowering IOP in a mammal, involving topical administration of an eye drop containing a selected compound of formula I, by administering a solution of an inactive or very weakly active phenylpropionate ester, which is hydrolyzed in the cornea to produce an active phenylpropionic acid in sufficient quantities to reduce IOP. However, upon systemic absorption, the inactive or weakly active ester does not exhibit systemic beta blocking action. In addition, the ester may be hydrolyzed by blood and tissue esterases to low concentrations of the corresponding acid, so as to produce little or no beta blocking effects.
5. Novel rapidly dissolving powder and tablet formulations of the ester compounds of formula I for oral administration.

The present invention concerns compounds and methods for providing rapid onset, short-duration beta-blockade in patients having coronary artery disease; for attenuating sympathetic nervous system hyperactivity or arrhythmia or migraine or ocular hypertension or anxiety including panic attack.

For systemic administration, the phenylpropionic acid compounds are administered intravenously or orally, whereas the ester form is administered orally. Upon oral administration, the ester compounds of formula I are rapidly absorbed and completely converted to the corresponding acid of formula I wherein R is hydrogen.

Pharmaceutical compositions for use in accordance with the present invention may be formulated in a conventional manner using one or more physiologically acceptable carriers or excipients. Thus, the compounds of Formula I and their physiologically acceptable salts and solvates may be formulated for oral or intravenous or topical ocular administration. The invention also describes a novel pharmaceutical formulation for oral administration of these compounds in the form of rapidly dissolving powder and tablets.

For oral administration, the pharmaceutical compositions may take the form of, for example, tablets or capsules prepared by conventional means with the pharmaceutically acceptable excipient such as binding agents (e.g., pregelatinized maize starch, polyvinylpyrrolidone or hydroxypropyl methylcellulose); fillers (e.g., lactose microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulfate). Liquid preparations for oral administration may be in the form of, for example, solutions, syrups or suspensions, or they may be presented as a dry product for constitution with water or other suitable vehicles before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparation may also contain buffer salts, flavoring, coloring and sweetening agents as appropriate. Preparations for oral administration may be suitably formulated to give controlled release of the active compound.

In order to prepare formulations suitable for intravenous administration of acids of formula I wherein R is hydrogen, solutions and suspensions are sterilized and are preferably isotonic to blood. In making injectable preparations, carriers which are commonly used in the field can be used, for example, water, ethyl alcohol, polyethylene glycol, ethoxylated isostearyl alcohol, polyoxylated isostearyl alcohol, polyoxyethylene sorbitol and sorbitate esters. In these instances, adequate amounts of sodium chloride, glucose or glycerin can be added to make the preparation isotonic.

Also described is a novel method for treating elevated IOP by topical administration of certain of these esters, which are inactive or very weakly active beta blockers. The esters of this type are advantageously administered topically to the eye in the form of a solution, ointment, or solid insert such as described in U.S. Pat. No. 4,195,085 to allow controlled or delayed release formulations. Formulations may contain the active compound, preferably in the form of a soluble acid addition salt. The dosage administered to a patient will depend upon the patients needs and the particular compounds employed.

Carriers used in the topical preparations of the present invention are preferably non-toxic pharmaceutical organic or inorganic compositions such as water, mixture of water and water miscible solvents, such as lower alcohols; mineral oils; petroleum jellies; ethyl cellulose; polyvinylpyrrolidone and other conventional carriers. In addition the pharmaceutical composition may contain, additional components such as emulsifying, preserving, wetting, and sterilizing agents. These include polyethylene glycols 200, 300, 400, and 600 carbowaxes 1,000, 1,500, 4,000, 6,000, and 10,000, bacteriocidal components such as quaternary ammonium compounds, phenylmercuric salts known to have cold sterilizing properties and which are non-injurious in use, thermosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan, monopalmitylate, diooctyl sodium sulfosuccinate, monothioglycerol, thiosorbitol, ethylenediaminetetraacetic acid, and the like. Additionally, suitable ophthalmic vehicle can be used as carrier media for the present purpose including conventional phosphate buffer vehicle systems, isotonic boric acid vehicles, isotonic sodium chloride vehicles, isotonic sodium borate vehicles and the like.

The method of treatment of this invention advantageously involves the topical administration of eye drops containing the active compound. Formulations for eye drops preferably include the active compounds as a soluble acid addition salt in a properly buffered sterile, aqueous isotonic solution.

The compounds of the invention are described by formula I and may exist as stereoisomers due to the presence of one or more asymmetric carbon atom(s). This invention includes all stereoisomeric forms as well as racemic mixture. The stereoisomer can be either resolved or separated or synthesized by known methods in the art.

Preferred acid compounds are those of formula I wherein W-Z represents isopropyl or t-butyl and Z represents NHCOR$_2$, wherein R$_2$ is isopropyl, N-morpholino, tetrahydrofuranyl, tetrahydropyranyl.

The most preferred acid compound is the compound of formula I wherein R is hydrogen and W-Z represents isopropyl.

Also preferred are ester compounds of formula I wherein W-Z represents isopropyl or t-butyl and Z represents NHCOR$_2$, wherein R$_2$ is isopropyl, tetrahydrofuranyl, tetrahydropyranyl and R is methyl, ethyl, n-propyl, cyclopropylmethyl, n-butyl, isobutyl or cyclopentyl.

The esters of formula I are synthesized by methods described in the literature. General methods for the preparation of the representative compounds of examples 1–8 are described in U.S. Pat. No. 4,387,103 issued on Jan. 7, 1983. General methods for the preparation of the representative compounds of examples 9–18 are described in U.S. Pat. No. 4,692,446 issued on Sep. 8, 1987.

The carboxylic acids of formula I wherein R is hydrogen, are prepared from the corresponding esters by standard methods, preferably by hydrolysis in aqueous acid or base or by alternative methods described in the literature (Compendium of organic synthetic methods, Vol. 1–8, Wiley-Interscience publication).

EXAMPLES 1–18

Specific preparation of the acid of formula I (wherein R is hydrogen and W-Z is isopropyl) from the ester of example 1 (Table 1) is described in example 19. The esters of example 2–18 (Tables 1 & 2) are similarly hydrolyzed to the corresponding acids (wherein R is hydrogen) by the procedure of Example 19.

TABLE 1

ESTERS OF FORMULA I

| EXAMPLE # | W-Z | R |
| --- | --- | --- |
| 1 | isopropyl | ethyl |
| 2 | isopropyl | n-propyl |
| 3 | isopropyl | cyclopropylmethyl |
| 4 | isopropyl | n-butyl |
| 5 | isopropyl | 2,2- dimethyl-1,3-dioxolane-5-methyl |
| 6 | t-butyl | methyl |
| 7 | t-butyl | isobutyl |
| 8 | t-butyl | cyclopentyl |

TABLE 2

ESTERS OF FORMULA I

| EXAMPLE # | W | Z= NHCOR$_2$, where R$_2$ is | R |
| --- | --- | --- | --- |
| 9 | C (CH$_3$)$_2$ CH$_2$ | isopropyl | cyclopropylmethyl |
| 10 | C (CH$_3$)$_2$ CH$_2$ | morpholino | n-propyl |
| 11 | C (CH$_3$)$_2$ CH$_2$ | 3-tetrahydrofuranyl | ethyl |
| 12 | C (CH$_3$)$_2$ CH$_2$ | isopropyl | isobutyl |
| 13 | C (CH$_3$)$_2$ CH$_2$ | morpholino | methyl |
| 14 | C (CH$_3$)$_2$ CH$_2$ | tetrahydropyranyl | n-butyl |
| 15 | C (CH$_3$)$_2$ CH$_2$ | tetrahydropyranyl | cyclopentyl |
| 16 | CH (CH$_3$) CH$_2$ | isopropyl | n-propyl |
| 17 | CH (CH$_3$) CH$_2$ | isopropyl | ethyl |
| 18 | C (CH$_3$)$_2$ CH$_2$ | 4-tetrahydrofuranyl | ethyl |

EXAMPLE 19

Preparation of (S)-(−) 3-[2-[2-hydroxy-3-(isopropylamino)propoxy]phenyl]propionic acid hydrochloride.

(S)-Ethyl 3-[2-[2-hydroxy-3-(isopropylamino)propoxy]phenyl]propionate hydrochloride (10 g, 0.029 moles) was dissolved in 6 N hydrochloric acid (200 mL). This solution was refluxed for 16 h and evaporated to dryness to give a white solid. This solid was dissolved in 50 mL of acetone with warming. Trace insoluble solid was removed by filtration through a fluted filter paper and the solution was allowed to cool to room temperature. The white crystalline solid which separated was filtered, washed with ether (2×25 mL) and air dried to give 6.2 g (0.0195 moles, 67.2%) of crude (S)-(−) 3-[2-[2-hydroxy-3-(isopropylamino)propoxy]phenyl]propionic acid hydrochloride, m.p. 123–124° C. The crude acid (7.5 g, 0.023 moles) was dissolved in hot acetone (40 mL) and allowed to cool at room temperature. The white crystalline solid which separated was filtered, washed with ether (50 mL) and recrystallized three times as described above. The product was then dried in vacuo to give 2.5 g (0.00786 moles, 34.1%) of (S)-(−) 3-[2-[2-hydroxy-3-(isopropylamino)propoxy]phenyl]propionic acid hydrochloride as a white crystalline powder; m.p. 125.9° C., Mass spec. (MS/MS) M+1, m/z 282.42.

EXAMPLE 20

A method of administration of the acid of example 19 by oral dosing with the ester of example 1 is described in this experiment. Four healthy volunteers were each given a single 100 mg oral dose of the compound (in the form of the rapidly dissolving powder) of (S)-Ethyl 3-[2-[2-hydroxy-3-(isopropylamino)propoxy]phenyl]propionate hydrochloride (of example 1) and blood samples were collected at 15, 30, 60, 120 and 240 minutes post-dose. The samples were analyzed to determine blood levels of the ester, Ethyl (S)-(−)-3-[2-[2-hydroxy-3-(isopropylamino)propoxy]phenyl]propionate and of the acid, (S)-(−) 3-[2-[2-hydroxy-3-(isopropylamino)propoxy]phenyl]propionic acid at various times after dosing, using a liquid chromatography-tandem mass spectrometry method. Results are shown in table 3.

TABLE 3

| Time (min) | 15 | 30 | 60 | 120 | 240 |
| --- | --- | --- | --- | --- | --- |
| Acid concentration (ng/mL) | 417 | 1329 | 1488 | 705 | 184 |
| Ester concentration (ng/mL) | 0 | 0 | 0 | 0 | 0 |

In conclusion, administration of a single 100 mg oral dose of the ester of example 1 to healthy volunteers delivers beta blocking concentrations of the acid of example 19 within 15 minutes. The acid is eliminated with a half-life of approximately 60 minutes. Only traces of the ester were measurable in the blood.

EXAMPLE 21

Demonstration of beta blocking activity by administration of the acid of example 19 via intravenous infusion is described in the following experiment.

One Beagle dog was anesthetized using Brevital (at 10 mg/kg, I.V.). Anaesthesia was maintained through artificial respiration with a mixture of oxygen and isoflurane (2.8%). A femoral artery was catheterized for blood pressure and heart rate recordings. The left and right femoral veins were catheterized for the administration of isoproterenol I.V. bolus dose (0.3 mg/kg ); the acid of example 19, and blood draws. Subdermal pin electrodes were positioned for the recording of Lead II Electrocardiogram (ECG). All recordings were made by a computerized recorder. After the animal stabilized, baseline values for mean arterial pressure (MAP), heart rate and Lead II ECG were established.

Prior to administration of the acid of example 19, isoproterenol was administered by I.V. bolus at a dose level which gave a 40–50% change from the pre-dose to the post dose agonist response in heart rate and arterial pressure. After reproducible responses to isoproterenol were obtained, the acid of example 19 was administered intravenously over a period of 20 minutes for each dose. The acid of example 19 was infused for 20 minutes at each dose and an isoproterenol challenge, I.V. bolus dose (0.3 mg/kg) was given every 10 minutes at each dose level. Heart rate and arterial pressure were measured before, during, and after each isoproterenol challenge. Blood samples (2–3 mL) were drawn from the femoral vein pre-dose and at 10 and 20 minutes post-dose for each treatment level prior to the administration of the isoproterenol. The blood samples were centrifuged, plasma placed in separate vials and frozen at −70° C.

The blood samples were processed and analyzed for blood concentration for the acid of example 19, using an LC/Tandem Mass Spectrometry method.

The percent inhibition of isoproterenol-induced tachycardia with increasing blood concentration of the acid is shown in figure 1. The percent inhibition increased linearly from 13% at a concentration of approximately 150 ng/mL to 93% at approximately 7000 ng/mL. The $IC_{50}$ (concentration causing 50% inhibition) was estimated at 800 ng/mL. The percent inhibition for the decrease in MAP (mean arterial pressure) increased from 0% at 150 ng/mL to 88% at approximately 7000 ng/mL. The $IC_{50}$ was estimated at 3000 ng/mL.

In conclusion, this study shows that the acid of example 19 is effective in inhibiting isoproterenol-induced tachycardia and MAP decrease in the dog. This compound inhibited the heart rate response at concentrations lower than those required for inhibition of the MAP response.

EXAMPLE 22

A proposed single bolus intravenous dose of the acids of formula I wherein R is hydrogen, for use according to the invention for administration to man (of approximately 70 kg body weight) is about 10 to 6000 microgm/kg, expressed as the weight of free base. A preferred single bolus dose of the acids of formula I wherein R is hydrogen, is about 100–1000 microgm/kg. The single dose may be administered, for example, 1 to 6 times per day. The dose will depend on the age and weight of the patient as well as the duration of effect required and severity of the condition to be treated.

EXAMPLE 23

A proposed single intravenous infusion of the acids of formula I wherein R is hydrogen, for use according to the invention for administration to man (of approximately 70 kg body weight) is about 0.1 to 100 microgm/kg/min, expressed as the weight of free base. A preferred intravenous infusion of the acids of formula I is about 1.0–10 microgm/kg/min. The dose will depend on the age and weight of the patient as well as the duration of effect required and severity of the condition to be treated.

EXAMPLE 24

A proposed single topical ocular dose of a solution of an inactive or very weakly active phenylpropionate ester of formula I for use according to the invention for administration to man (of approximately 70 kg body weight) is about 0.1–10.0%, expressed as the weight of free base. A preferred single topical ocular dose of phenylpropionate esters of formula I is about 0.25–5.0%. The single dose may be administered, for example, 1 to 6 times per day. Unit dosages of the active compound can range from about 0.001 to about 5.0 mg, preferably from about 0.05 to about 2.5 mg. The dose will depend on the age and weight of the patient as well as the duration of effect required and severity of the condition to be treated.

EXAMPLE 25

Specific formulations for rapidly dissolving powders and tablets of (S)-Ethyl 3-[2-[2-hydroxy-3-(isopropylamino)

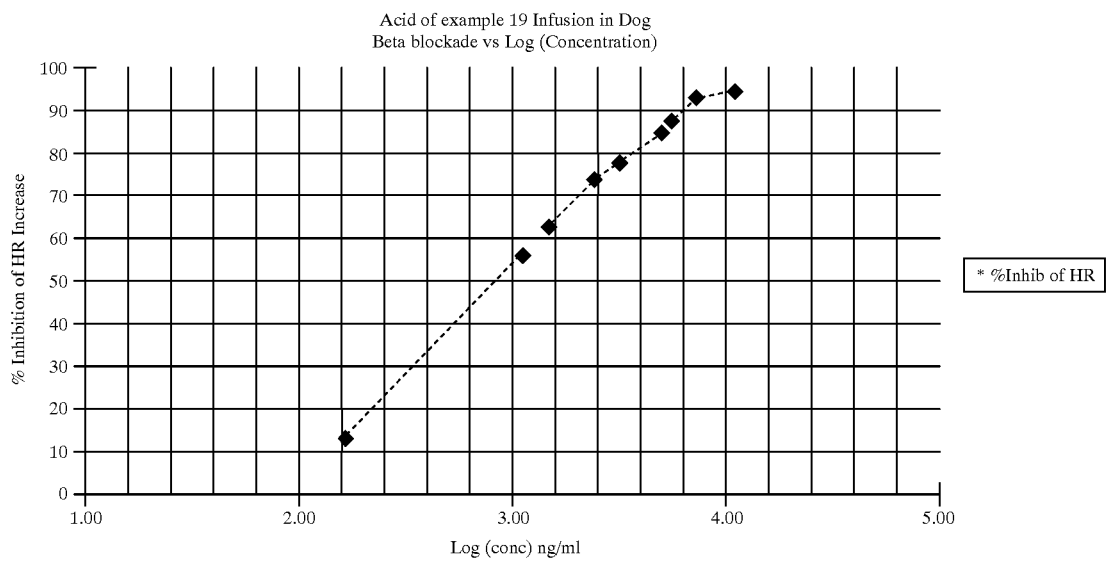

FIG. I propoxy]phenyl]propionate (example 1) are as follows:

| Ingredients | Range % w/w | Preferred Range % w/w |
|---|---|---|
| (S)-Ethyl 3-[2-[2-hydroxy-3-(isopropylamino)propoxy]phenyl]propionate hydrochloride (example 1) | 10–40% | 20–30% |
| Lactose Monohydrate | 30–70% | 40–50% |
| Crospovidone | 5–18% | 7–14% |
| Sodium bicarbonate | 0–5% | 2–4% |
| Magnesium Stearate | 0.25–2.5% | 0.5–1.0% |
| SiO2 | 0–1.0% | 0–0.5% |

An appropriate amount of a sweetener(s) and/or a flavor(s) may be added if needed to mask an unpleasant taste, if any.

(S)-Ethyl 3-[2-[2-hydroxy-3-(isopropylamino)propoxy]phenyl]propionate hydrochloride is mixed with the appropriate excipient, in a blender until blend uniformity is achieved. This powder blend is packaged in appropriate size units in bottles, dosage container or powder paper for administration.

The tablets are manufactured by conventional tableting equipment using the powder. The physical properties of the tablets are preferably with in the range shown below:

| Tests on the tablet | Range | Preferred range |
|---|---|---|
| Hardness in kp (Kilo Pascal) | 2–5 | 2–3 |
| Disintegration in Minutes | 0.25–2.5 | <1 |
| 70% Dissolution in Minutes | <2.0 | 0.5–5 |

The dissolution (USP 23<711>) and disintegration test (USP 23<701>) were performed according to USP methods.

What is claimed:

1. A compound of the formula I:

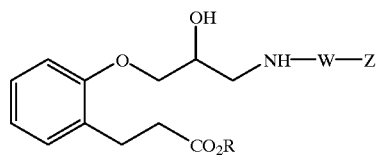

Formula I

Wherein

R represents hydrogen;

W represents $CH(CH_3)CH_2$—, $C(CH_3)_2CH_2$—;

Z represents hydrogen, —$NHCOR_2$, —$NHCONR_2R_3$ or —$NHSO_2R_2$ or —$NHSO_2NR_2R_3$ or —$NHCOOR_4$ wherein $R_4$ is alkyl of from 1 to about 6 carbon atoms, alkoxyalkyl wherein the alkyl groups may be the same or different and contain from 1 to about 6 carbon atoms, alkoxyaryl, cycloalkyl of from 3 to about 8 carbon atoms. $R_2$ and $R_3$ may be the same or different and represent hydrogen, alkyl of from 1 to about 6 carbon atoms, alkoxyalkyl wherein the alkyl groups may be the same or different and contain from 1 to about 6 carbon atoms, alkoxyaryl, cycloalkyl of from 3 to about 8 carbon atoms, a phenyl group substituted or unsubstituted, heteroaryl, furanyl, thiophenyl, imidazolyl, oxazolyl or indolyl or tetrahydrofuranyl, tetrahydropyranyl, dioxanyl, 2,2-dimethyl dioxolane-5-methyl, pyrrolidinyl, piperazinyl and tetrahydrooxazolyl, aralkyl except that $R_2$ and $R_3$ are not hydrogen when Z is —$NHSO2R_2$, or $R_2$ and $R_3$ may together with N form a 5 to 7 membered heterocyclic group; and pharmaceutically acceptable salts thereof.

2. A compound of claim 1 wherein W-Z represents an isopropyl or a t-butyl group.

3. A compound of claim 1 wherein W-Z represents an isopropyl group.

4. A compound of claim 1 wherein Z represents —$NHCOR_2$, where $R_2$ is isopropyl, tetrahydrofuranyl, tetrahydropyranyl or —$NHCONR_2R_3$; wherein $R_2$ and $R_3$ together with N form a morpholino group.

5. A compound of the formula I:

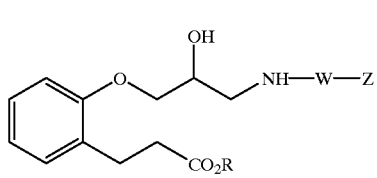

Formula I

Wherein

R represents C-3 to C-6 cycloalkyl or C-4 to C-10 straight or branched carbon chain alkyl-cycloalkyl or a group —B—D, where B is C-2 to C-10 straight or branched carbon chain alkyl and D is hydroxy or alkyloxy or 2,3-dihydroxypropyl or 2,3-dialkyloxypropyl or 2,2-dialkyl-1,3-dioxolane-5-methyl, where alkyl is C-1 to C-10 straight or branched carbon chain;

W represents $CH(CH_3)CH_2$—, $C(CH_3)_2CH$—;

Z represents hydrogen, —$NHCOR_2$, —$NHCONR_2R_3$ or —$NHSO_2R_2$ or —$NHSO_2NR_2R_3$ or —$NHCOOR_4$ wherein $R_4$ is alkyl of from 1 to about 6 carbon atoms, alkoxyalkyl wherein the alkyl groups may be the same or different and contain from 1 to about 6 carbon atoms, alkoxyaryl, cycloalkyl of from 3 to about 8 carbon atoms. $R_2$ and $R_3$ may be the same or different and represent hydrogen, alkyl of from 1 to about 6 carbon atoms, alkoxyalkyl wherein the alkyl groups may be the same or different and contain from 1 to about 6 carbon atoms, alkoxyaryl, cycloalkyl of from 3 to about 8 carbon atoms, a phenyl group substituted or unsubstituted, heteroaryl, furanyl, thiophenyl, imidazolyl, oxazolyl or indolyl or tetrahydrofuranyl, tetrahydropyranyl, dioxanyl, 2,2-dimethyl dioxolane-5-methyl, pyrrolidinyl, piperazinyl and tetrahydrooxazolyl, aralkyl except that $R_2$ and $R_3$ are not hydrogen when Z is —$NHSO_2R_2$, or $R_2$ and $R_3$ may together with N form a 5 to 7 membered heterocyclic group; and pharmaceutically acceptable salts thereof.

6. A method of inducing beta-blockade in a patient for the treatment or prophylaxis of diseases states which are responsive to attenuation of sympathetic nervous system activity or beta adrenergic blockade, the method comprising administering to such patient a compound of the formula I; by intravenous or oral administration:

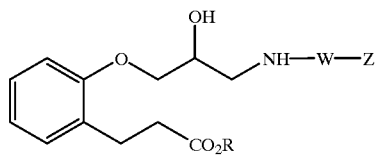

Formula I

Wherein
  R represents hydrogen;
  W represents $CH(CH_3)CH_2—$, $C(CH_3)_2CH_2—$;
  Z represents hydrogen, $—NHCOR_2$, $—NHCONR_2R_3$ or $—NHSO_2R_2$ or $—NHSO_2NR_2R_3$ or $—NHCOOR_4$, wherein
  $R_4$ is alkyl of from 1 to about 6 carbon atoms, alkoxyalkyl wherein the alkyl groups may be the same or different and contain from 1 to about 6 carbon atoms, alkoxyaryl, cycloalkyl of from 3 to about 8 carbon atoms;
  $R_2$ and $R_3$ may be the same or different and represent hydrogen, alkyl of from 1 to about 6 carbon atoms, alkoxyalkyl wherein the alkyl groups may be the same or different and contain from 1 to about 6 carbon atoms, alkoxyaryl, cycloalkyl of from 3 to about 8 carbon atoms, a phenyl group substituted or unsubstituted, heteroaryl, furanyl, thiophenyl, imidazolyl, oxazolyl, indolyl, tetrahydrofuranyl, tetrahydropyranyl, dioxyanyl, 2,2-dimethyl dioxolane-5-methyl, pyrrolidinyl, piperazinyl, tetrahydrooxazolyl, and aralkyl except that $R_2$ and $R_3$ are not hydrogen when Z is $NHSO_2R_2$, or $R_2$ and $R_3$ may together with N form a 5 to 7 membered heterocyclic group; and pharmaceutically acceptable salts thereof.

7. The method of claim 6 wherein W-Z represents an isopropyl or a t-butyl group.

8. The method of claim 6 wherein W-Z represents an isopropyl group and R is ethyl.

9. The method of claim 6 wherein Z represents $—NHCOR_2$, where $R_2$ is isopropyl, tetrahydrofuranyl, tetrahydropyranyl or $—NHCONR_2R_3$, wherein $R_2$ and $R_3$ together with N form a morpholino group.

10. The method of claim 6 wherein the compound is administered by intravenous administration.

11. The method of claim 10 wherein W-Z represents an isopropyl or a t-butyl group.

12. The method of claim 10 wherein W-Z represents an isopropyl group.

13. The method of claim 10 wherein Z represents $—NHCOR_2$, where $R_2$ is isopropyl, tetrahydrofuranyl, tetrahydropyranyl or $—NHCONR_2R_3$; wherein $R_2$ and $R_3$ together with N form a morpholino group.

14. The method of claim 10 wherein the compound has a systemic half life of about 30 to 120 minutes.

15. The method of claim 14 wherein W-Z represents an isopropyl or a t-butyl group.

16. The method of claim 14 wherein W-Z represents an isopropyl group.

17. The method of claim 14 wherein Z represents $—NHCOR_2$, where $R_2$ is isopropyl, tetrahydrofuranyl, tetrahydropyranyl or $—NHCONR_2R_3$; wherein $R_2$ and $R_3$ together with N form a morpholino group.

18. The method of claim 6 wherein the compound is administered by oral administration.

19. The method of claim 18 wherein W-Z represents an isopropyl or a t-butyl group.

20. The method of claim 18 wherein W-Z represents an isopropyl group.

21. The method of claim 18 wherein Z represents $—NHCOR_2$, where $R_2$ is isopropyl, tetrahydrofuranyl, tetrahydropyranyl or $—NHCONR_2R_3$; wherein $R_2$ and $R_3$ together with N form a morpholino group.

22. A method of inducing beta-blockade in a patient for the treatment or prophylaxis of diseases states which are responsive to attenuation of sympathetic nervous system activity or beta adrenergic blockade namely: coronary artery disease including myocardial ischemic disorders, angina and myocardial infarction; arrhythmia; hypertension; anxiety including panic attack; migraine or glaucoma comprising administering by oral administration to such patient a compound of the formula:

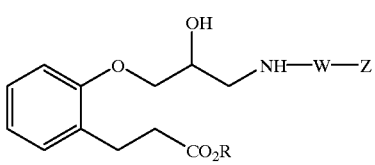

Formula I

Wherein
  R represents C-1 to C-10 straight or branched carbon chain alkyl or C-3 to C-6 cycloalkyl or C-4 to C-10 straight or branched carbon chain alkyl-cycloalkyl or a group —B—D, where B is C-2 to C-10 straight or branched carbon chain alkyl and D is hydroxy or alkyloxy or 2,3-dihydroxypropyl or 2,3-dialkyloxypropyl or 2,2-dialkyl-1,3-dioxolane-5-methyl, where alkyl is C-1 to C-10 straight or branched carbon chain;
  W represents $CH(CH_3)CH_2—$, $C(CH_3)_2CH_2—$;
  Z represents hydrogen, $—NHCOR_2$, $—NHCONR_2R_3$ or $—NHSO_2R_2$ or $—NHSO_2NR_2R_3$ or $—NHCOOR_4$ wherein $R_4$ is alkyl of from 1 to about 6 carbon atoms, alkoxyalkyl wherein the alkyl groups may be the same or different and contain from 1 to about 6 carbon atoms, alkoxyaryl, cycloalkyl of from 3 to about 8 carbon atoms. $R_2$ and $R_3$ may be the same or different and represent hydrogen, alkyl of from 1 to about 6 carbon atoms, alkoxyalkyl wherein the alkyl groups may be the same or different and contain from 1 to about 6 carbon atoms, alkoxyaryl, cycloalkyl of from 3 to about 8 carbon atoms, a phenyl group substituted or unsubstituted, heteroaryl, furanyl, thiophenyl, imidazolyl, oxazolyl or indolyl or tetrahydrofuranyl, tetrahydropyranyl, dioxanyl, 2,2-dimethyl dioxolane-5-methyl, pyrrolidinyl, piperazinyl and tetrahydrooxazolyl, aralkyl except that $R_2$ and $R_3$ are not hydrogen when Z is $—NHSO2R_2$, or $R_2$ and $R_3$ may together with N form a 5 to 7 membered heterocyclic group; and pharmaceutically acceptable salts thereof.

23. The method claim 22 wherein R represents methyl, ethyl, n-propyl or n-butyl group.

24. The method of claim 22 wherein W-Z represents isopropyl group; R represents ethyl group.

25. The method of claim 22 wherein Z represents $—NHCOR_2$, where $R_2$ is isopropyl, tetrahydrofuranyl, tetrahydropyranyl or $—NHCONR_2R_3$; wherein $R_2$ and $R_3$ together with N form a morpholino group.

26. The method of claim 22 wherein the compound is rapidly absorbed to produce therapeutic levels of the metabolite acid within about 15 to 30 minutes of administration.

27. The method of claim 26 wherein W-Z represents an isopropyl or a t-butyl group.

28. The method of claim 26 wherein W-Z represents an isopropyl group and R is ethyl.

29. The method of claim 26 wherein Z represents —NHCOR$_2$, where R$_2$ is isopropyl, tetrahydrofuranyl, tetrahydropyranyl or —NHCONR$_2$R$_3$; wherein R$_2$ and R$_3$ together with N form a morpholino group.

30. The method of claim 22 wherein the compound undergoes essentially complete first-pass metabolism to produce therapeutic levels of the metabolite acid within about 15 to 30 minutes of administration.

31. The method of claim 30 wherein W-Z represents an isopropyl or a t-butyl group.

32. The method of claim 30 wherein W-Z represents an isopropyl group and R is ethyl.

33. The method of claim 30 wherein Z represents —NHCOR$_2$, where R$_2$ is isopropyl, tetrahydrofuranyl, tetrahydropyranyl or —NHCONR$_2$R$_3$; wherein R$_2$ and R$_3$ together with N form a morpholino group.

34. A method of treating glaucoma or lowering intraocular pressure in a patient in need of such treatment comprising administering by a topical ocular dose of a solution of an inactive or weakly active phenylpropionate esters of formula I:

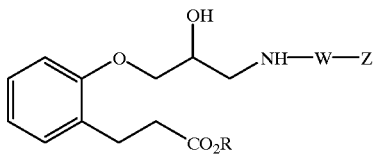

Formula I

Wherein

R represents C-3 to C-6 cycloalkyl or C-4 to C-10 straight or branched carbon chain alkyl-cycloalkyl or a group —B—D, where B is C-2 to C-10 straight or branched carbon chain alkyl and D is hydroxy or alkyloxy or 2,3-dihydroxypropyl or 2,3-dialkyloxypropyl or 2,2-dialkyl-1,3-dioxolane-5-methyl, where alkyl is C-1 to C-10 straight or branched carbon chain;

W represents CH(CH$_3$)CH$_2$—, C(CH$_3$)$_2$CH$_2$—;

Z represents hydrogen, —NHCOR$_2$, —NHCONR$_2$R$_3$ or —NHSO$_2$R$_2$ or —NHSO$_2$NR$_2$R$_3$ or —NHCOOR$_4$ wherein R$_4$ is alkyl of from 1 to about 6 carbon atoms, alkoxyalkyl wherein the alkyl groups may be the same or different and contain from 1 to about 6 carbon atoms, alkoxyaryl, cycloalkyl of from 3 to about 8 carbon atoms. R$_2$ and R$_3$ may be the same or different and represent hydrogen, alkyl of from 1 to about 6 carbon atoms, alkoxyalkyl wherein the alkyl groups may be the same or different and contain from 1 to about 6 carbon atoms, alkoxyaryl, cycloalkyl of from 3 to about 8 carbon atoms, a phenyl group substituted or unsubstituted, heteroaryl, furanyl, thiophenyl, imidazolyl, oxazolyl or indolyl or tetrahydrofuranyl, tetrahydropyranyl, dioxanyl, 2,2-dimethyl dioxolane-5-methyl, pyrrolidinyl, piperazinyl and tetrahydrooxazolyl, aralkyl except that R$_2$ and R$_3$ are not hydrogen when Z is —NHSO2R$_2$, or R$_2$ and R$_3$ may together with N form a 5 to 7 membered heterocyclic group; and pharmaceutically acceptable salts thereof.

35. The method of claim 34 wherein W-Z represents an isopropyl or a t-butyl group.

36. The method of claim 34 wherein W-Z represents an isopropyl group.

37. The method of claim 34 wherein Z represents —NHCOR$_2$, where R$_2$ is isopropyl, tetrahydrofuranyl, tetrahydropyranyl or —NHCONR$_2$R$_3$; wherein R$_2$ and R$_3$ together with N form a morpholino group.

* * * * *